(12) United States Patent
Nilsson (10) Patent No.: US 7,476,211 B2
(45) Date of Patent: Jan. 13, 2009

(54) SYSTEM AND METHOD FOR PHYSIOLOGICAL DRAINAGE

(75) Inventor: Per Erik Nilsson, Höllviken (SE)

(73) Assignee: Technovobis AB, Malmo (SE)

( * ) Notice: Subject to any disclaimer, the term of this patent is extended or adjusted under 35 U.S.C. 154(b) by 368 days.

(21) Appl. No.: 10/415,397

(22) PCT Filed: Oct. 26, 2001

(86) PCT No.: PCT/SE01/02362

§ 371 (c)(1), (2), (4) Date: Dec. 8, 2003

(87) PCT Pub. No.: WO02/36193

PCT Pub. Date: May 10, 2002

(65) Prior Publication Data

US 2004/0087887 A1    May 6, 2004

(30) Foreign Application Priority Data

Oct. 30, 2000 (NO) .................................. 20005469

(51) Int. Cl.
*A61M 5/00* (2006.01)
*A61M 37/00* (2006.01)
(52) U.S. Cl. .................. 604/8; 604/9; 604/6.16
(58) Field of Classification Search ............. 604/8–10, 604/523, 264, 284, 4.01–6.16, 30–35, 43–49, 604/93, 115, 167
See application file for complete search history.

(56) References Cited

U.S. PATENT DOCUMENTS

| | | | |
|---|---|---|---|
| 3,738,365 A | 6/1973 | Schulte | |
| 3,769,982 A | 11/1973 | Schulte | |
| 3,877,429 A * | 4/1975 | Rasumoff | 604/158 |
| 3,894,541 A * | 7/1975 | El-Shafei | 604/10 |
| 4,122,858 A | 10/1978 | Schiff | |
| 4,631,051 A | 12/1986 | Harris | |
| 4,655,745 A | 4/1987 | Corbett | |
| 4,767,400 A | 8/1988 | Miller et al. | |
| 5,207,684 A | 5/1993 | Nobles | |
| 5,385,541 A * | 1/1995 | Kirsch et al. | 604/8 |
| 5,618,270 A | 4/1997 | Orejola | |
| 6,045,547 A * | 4/2000 | Ren et al. | 604/525 |
| 6,086,565 A * | 7/2000 | Ouchi | 604/187 |

FOREIGN PATENT DOCUMENTS

| | | |
|---|---|---|
| EP | 1040844 | 10/2000 |
| JP | 54-21089 | 2/1979 |
| JP | 11-319086 | 11/1999 |

* cited by examiner

Primary Examiner—Leslie R. Deak
Assistant Examiner—Phil Wiest
(74) Attorney, Agent, or Firm—Ladas & Parry LLP (57) ABSTRACT

A device (A) can be used to create a new channel to conduct fluid from a fluid-conducting catheter to a blood vessel without contact between the device or the catheter and the blood flow in the blood vessel. The device includes an outer and an inner tube-like part; in use, the tube-like parts are joined with essentially parallel axes, The outer tube-like part has a lengthwise slit along part of its length to let part of the blood vessel enter and, with the inner tube-like part, to form the new channel. The inner tube-like part is in part to be connected to the catheter. The device may be used to connect a CSF conducting catheter to the deep neck vein of a human. Also, an applicator device and a support instrument used to facilitate a surgical procedure of applying the device are described.

12 Claims, 7 Drawing Sheets

SYSTEM AND METHOD FOR PHYSIOLOGICAL DRAINAGE

FIELD OF INVENTION

This invention concerns a device to be applied on a blood vessel in such a way that it creates a new channel together with the vessel. The new channel runs essentially parallel with the vessel and conducts fluid from a fluid-conducting catheter to the blood vessel without contact between the device or the fluid conducting catheter and the blood flow in the vessel. The invention also comprises an instrument for the application of the device and a support instrument for the vessel during an operation connected to the application. Such a device is of particular use when treating (shunting) hydrocephalus, where it is desirable to create a channel to conduct CSF (cerebrospinal fluid) from the fluid conducting catheter to the deep neck vein without contact between the device, the catheter or any foreign body and the blood flow in the vessel.

The invention also comprises the use of such an invention to connect the CSF conducting catheter to the human deep neck vein and a way to apply the device.

BACKGROUND

In individual patients the natural resorption of CSF is blocked or reduced because of malformation or following bleeding or infection. If the missing natural resorption is not compensated for the patient will develop hydrocephalus (increased intracranial pressure with brain damage). To avoid this the patient usually needs a lifelong drainage of CSF to the venous system or the abdomen.

When the infusion of fluid in the venous system is long-lasting as when shunting hydrocephalus there is an increased risk of thrombosis or infection caused by the foreign material of the catheter. Thrombosis lead to stop in the blood flow and infection makes it necessary to remove the catheter and treat with antibiotics before putting in a new catheter. The problem with thrombosis is reduced by letting the fluid conducting catheter end in the right atrium of the heart where the fast blood flow reduces the risk of thrombosis, but the risk for infection is still the same.

In the end of the 50's, when useful materials for catheters and pressure regulating valves became available, the most common method became draining CSF to the heart. When draining to the heart the catheter runs from the ventricular system of the brain under the skin and via a pressure or flow regulating valve that prevents backflow and further down under the skin into the deep neck vein and into the right atrium of the heart. Trials have been done where the catheter has been connected to a narrow branch of the neck vein in the hope that the fluid from the brain would prevent contact between the catheter and the blood. However, this did not function well.

To be able to regulate the blood flow from the brain and the pressure in the brain the veins in the neck are soft and have a variable volume. This results in back flow of blood, thrombosis and stop of the flow when the catheter ends in the blood in such a vein.

Today the usual method is draining to the abdomen. This removes the risk of thrombosis and is of great advantage when shunting children, as a long catheter in the abdomen can compensate for growth. In adult patients, draining to the abdomen has an important disadvantage with overdrainage and siphon effect caused by the increased pressure gradient in upright position compared with lying down. This problem is not fully solved by using antsiphon valves or other types of pressure and flow regulating valves. Another disadvantage in shunting to the abdomen is that abdominal disease, especially infection, may hinder the use of the shunt.

Obviously there exists a need to improve the methods now in use for shunting hydrocephalus. The ideal method would be to drain CSF to the sagittal sinus, the stiff vein in the middle inside the skull bone, and trials with this are in progress. However, with the conventional shunt systems of today it should be easier and less risky to find a way to drain to the deep neck vein and from there to the heart, but then without contact between the blood and any foreign material. In this way a catheter in the heart would be avoided as well as the use of X-ray, ECG or other means for this positioning.

Prior art includes a number of patent documents. U.S. Pat. No. 3,894,541 (El-Shafei et al.) discloses a method of treating hydrocephaulus preventing the contact between a shunting catheter and the circulating blood by inserting a venous end of a venous catheter into the proximal segment of the ligated neck vein against the direction of blood flow. U.S. Pat. No. 3,738,365 (Schulte) discloses an extensible catheter comprising a flexible metallic helical spring and slidable conduit sections. U.S. Pat. No. 3,769,982 (Schulte) discloses a physiological drainage system with closure means responsive to downstream suction comprising a flexible diaphragm extending across a control cavity.

SUMMARY OF THE INVENTION

Therefore an object of the present invention is to provide a device for conducting fluid from a fluid-conducting catheter to a blood vessel without contact between the device or the catheter and the blood flow in the vessel and to provide instrumentation for the application and a method for applying the device. When there is no contact between the blood and the foreign material the risk of thrombosis is diminished and infection is reduced.

In accordance with the invention this object is obtained by the means of the features of the device that are evident in the independent claim 1 as filed, of the applicator in claim 12 as filed, of the support instrument in claim 15 as filed, and of the method of applying in claim 13 as filed. Additional objectives and advantages are provided by means of the features in the dependent claims.

The invention concerns a device that can be used to conduct fluid, preferentially CSF, from a fluid-conducting catheter to a blood vessel without contact between the device or the catheter and the blood flow in the blood vessel. This can be obtained by applying the device on a blood vessel in such a way that a part of this blood vessel, in cross section, creates a new, narrow channel with invariable volume and essentially running in parallel with the length of the blood vessel and the blood flow. CSF flows into this channel via a fluid-conducting catheter that is connected to the device and out of this channel via its opening into the vein. Because the channel has a constant volume and is filled with CSF the blood flowing in the blood vessel is prevented from passing into the new channel and come in contact with the device.

Part of the inventive concept is also an integral support instrument for capturing and compressing a vessel during the operation, comprising a handle member that has an elongated handle member connected to a fork-like vessel-capturing element having a first and a second prong; wherein the first prong is essentially U-shaped, and the second prong is shorter than said first prong and being essentially L-shaped, and wherein a vessel-capturing slit is formed between said prongs.

BRIEF DESCRIPTION OF THE DRAWINGS

The following section describes preferred embodiments of the invention in detail, with reference to the accompanying drawings.

FIG. 1a shows a midline section of the preferred design of the device according to the invention, seen from the side;

FIG. 1b shows a cross section of the device in FIG. 1a, along the line S-S in FIG. 1a;

FIG. 3 shows the outer tube-like part of the device, a) from the side, b) seen from below, c) seen from above;

FIG. 4 illustrates the resulting blood vessel channel after applying the device, a) midline section, b) cross section;

FIG. 10a show in perspective a support instrument for keeping a vessel in place during an operation.

FIG. 10b shows in a view from above a detail of a fork-like element of the instrument in FIG. 10a.

FIG. 10c shows in a side view, the instrument of FIG. 10a.

DETAILED DESCRIPTION OF PREFERRED EMBODIMENTS

FIG. 1a shows a midline section of a preferred design of device A according to the invention.

The device A is composed of two parts: one outer tube-like part 1 with a first 3 and a second 4 end and one inner tube-like part 2 with a first 5 and a second 6 end. The two tube-like parts are essentially concentric and parallel. The two tube-like parts 1 and 2 are joined near the first end 3 of the outer tube-like part 1 and at an intermediate part 7 of the inner tube-like part 2.

FIG. 1b shows a cross section of the device A along the line S-S in FIG. 1a. Here it is obvious that the two tube-like parts 1 and 2 are concentric. It is also obvious that the outer tube-like part 1 has a lengthwise slit 8, which will be mentioned later on.

Figure 2:
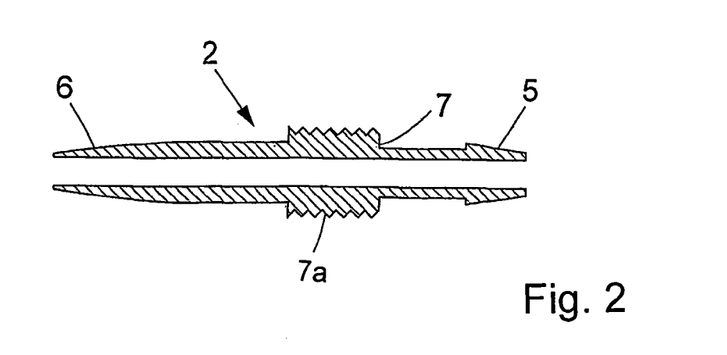
FIG. 2 shows a midline section of the inner tube-like part of the device, seen from the side.

FIG. 2 shows in closer detail a midline section of an embodiment of the inner tube-like part 2. Inner tube-like 2 is essentially axially symmetric with exception for the thread 7a of screw on the intermediate part 7.

The first end 5 of the inner tube-like part 2 is arranged to be connected to a fluid-conducting catheter. In the shown design, this is achieved by shaping the first end 5 of the inner tube-like part as an external nipple.

The second end 6 of the inner tube-like part 2 is designed to facilitate its passing through an opening in the vessel wall and at the same time give a close connection between the blood vessel wall and said inner tube-like part 2. This is achieved by making the inner tube-like part 2 slightly conical near its second end 6, pointing to its second end 6.

The outer tube-like part 1 and the inner tube-like part 2 are in the illustrated embodiment joined with threads 3a, 7a. The inner tube-like part 2 is supplied with external threads 7a along the outer intermediate part 7, and the outer tube-like part 1 is supplied with corresponding internal threads 3a at an internal part close to the first end 3 of the outer tube-like part 1.

Alternatively, the outer tube-like part 1 and the inner tube-like part 2 can be joined by conical surfaces. In this case the inner tube-like part 2 has a slightly conical form pointing either to its first end 5 or its second end 6, while the outer tube-like part 1 at its first end 3 has a corresponding internal conical form.

The two parts can if desired also be joined by glue.

As yet another alternative, the outer tube-like part 1 and the inner tube-like part 2 can be solidly joined from the beginning, instead of being two parts meant to join later on. The device has been designed to be possible to manufacture in one piece by injection moulding.

However, there are some advantages to make the device A in two separate parts, as it may allow simple manufacturing and combination of different materials and designs.

Figure 3:
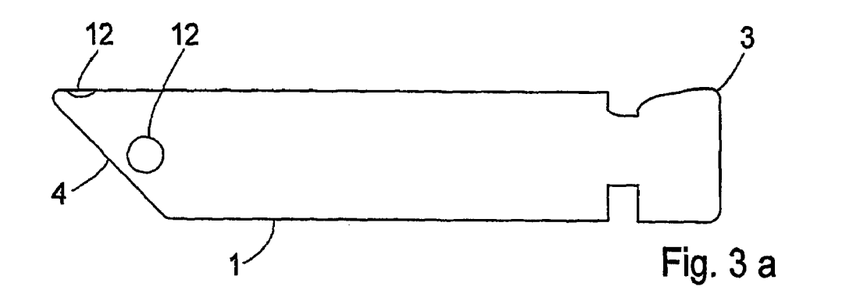

FIG. 3a)-c) shows in closer detail the outer tube-like part 1 of the device seen from a) the side, b) from below, c) from above.

The outer tube-like part 1 has along a part of its length from its second end 4 a lengthwise slit 8 for entrance of a corresponding length of the blood vessel, as shown in FIG. 3b.

Figure 1:
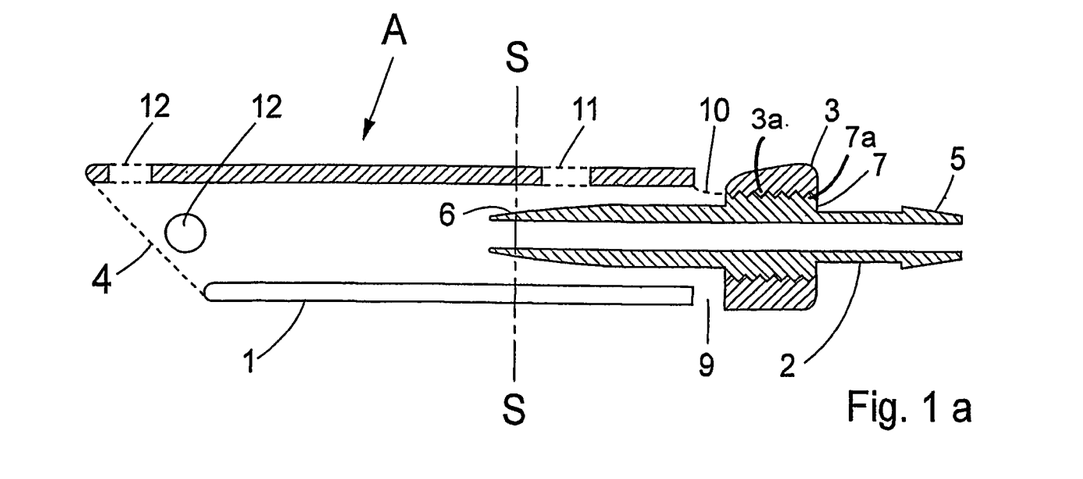

When the outer tube-like part 1 and inner tube-like part 2 are joined, as illustrated in FIG. 1, the second end 6 of the inner tube-like part 2 is wholly or partly surrounded by the lengthwise slit equipped part of the outer tube-like part 1.

Figure 4:
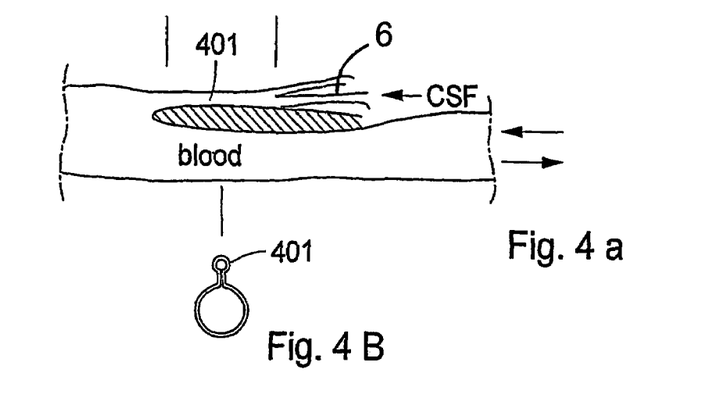

The lengthwise slit 8 has essentially a width corresponding to double the thickness of the blood vessel wall. The intention with the lengthwise slit 8 is to limit, in the cross section, the part of the blood vessel that enters the lengthwise slit 8. This part of the blood vessel will, before it enters the lengthwise slit 8, be punctured in such a way (see procedure FIG. 6) that the second end 6 of the inner tube-like part 2 can pass the blood vessel wall in this part of the blood vessel when the blood vessel enters the lengthwise slit 8. After this, the inner tube-like part 2 from the second end 6 to the intermediate part 7 will be inside the part of the blood vessel that has entered the lengthwise slit 8. In this way, as well as by the moulding effect of an infusion needle 24 when glue is injected (see procedure FIG. 6-8) a new narrow and stiff channel will be created along the blood vessel, constituting a channel of living tissue from the second end 6 of the inner tube-like part 2 to the second end 4 of the outer tube-like part. FIG. 4a shows the appearance of the new channel 401 when the device A has been applied on a blood vessel. The outer tube-like part 1 has been removed in the drawing for reasons of clarity. FIG. 4b shows the same situation in cross section.

After the device A has been applied on a blood vessel there is thus a double blood vessel wall in lengthwise slit 8, part of the circumference as well as part of the length (corresponding to the length of the lengthwise slit 8) of the blood vessel is situated inside the outer tube-like part 1. The second end 6 of the inner tube-like part 2 passes the blood vessel wall that is inside the outer tube-like part 1. The width of lengthwise slit 8 is enough for nutrition of the vessel wall inside outer tube-like part 1, but does not allow fluid to pass through i.e. between, the compressed vessel walls in the lengthwise slit 8. Too narrow a slit will prevent nutrition and too wide a slit will allow blood to pass through and come into contact with foreign material (the second end 6 of the inner tube-like part 2).

The second end 4 of the outer tube-like part 1 is cut oblique in such a way that the side running alongside lengthwise slit 8 is the shortest. This facilitates passing of the device onto the blood vessel and gives a better anatomy for passage of the new channel into the blood vessel (the deep neck vein). The outer tube-like part 1 has two cross openings 9 and 10 near its first end 3. The cross opening 9 is joined with and crosses the lengthwise slit 8, and the other cross opening 10 is arranged opposite the cross opening 9. The cross opening 10 is featured in the same way. All edges and corners are rounded to adjust to the anatomy of the tissue.

The cross openings 9 and 10 give opportunity to fix the blood vessel wall to the device with one or more sutures. The cross opening 10 can also, if desirable, serve as an opening for a suture thread tied to the blood vessel. This makes it possible to pull the blood vessel wall in between the inner tube-like part 2 and the outer tube-like part 1 of the device. Said cross opening 10 can also be used to check that the blood vessel wall is in the proper position and that the glue flows out as intended. The glue used is preferably Tisseel®, a two-component glue. The fibrinogen and the thrombin of such a glue give a rubberlike tissue that is later organised as the surrounding tissue.

The second end 4 of the outer tube-like part 1 has at least one hole 12 to allow fixing the blood vessel wall to the outer tube-like part 1 with suture. The glue will also fix the blood vessel wall to the inside of the outer tube-like part 1 partly by adhering directly to the inside of the outer tube-like part 1, partly by filling the cross openings and/or holes 9-12 of the outer tube-like part 1, thereby mechanically fixing the blood vessel to said outer tube-like part 1.

The outer tube-like part 1 has an additional hole 11 to fix the device A to the applicator (at the end of a glue conducting tube 27) and to apply glue. As the glue is injected from the syringe on the applicator it passes hole 11 and fills the space between the inside of the outer tube-like part 1 and the blood vessel wall.

Preferably, the whole device A is made out of film tissue-compatible materials like plastics, nylon, ceramics or metals. A suitable plastic is polyetheretherketone (PEEK). The various parts can be made out of different materials that are firm and compatible. It is an advantage if the material used is resistant and stable to allow repeated sterilization procedures, e.g. to withstand steam and air at 140° C., to allow sterilization by heat and/or to resist ethylene oxide at 50 degrees Celsius as this is another procedure of sterilization.

Figure 5:
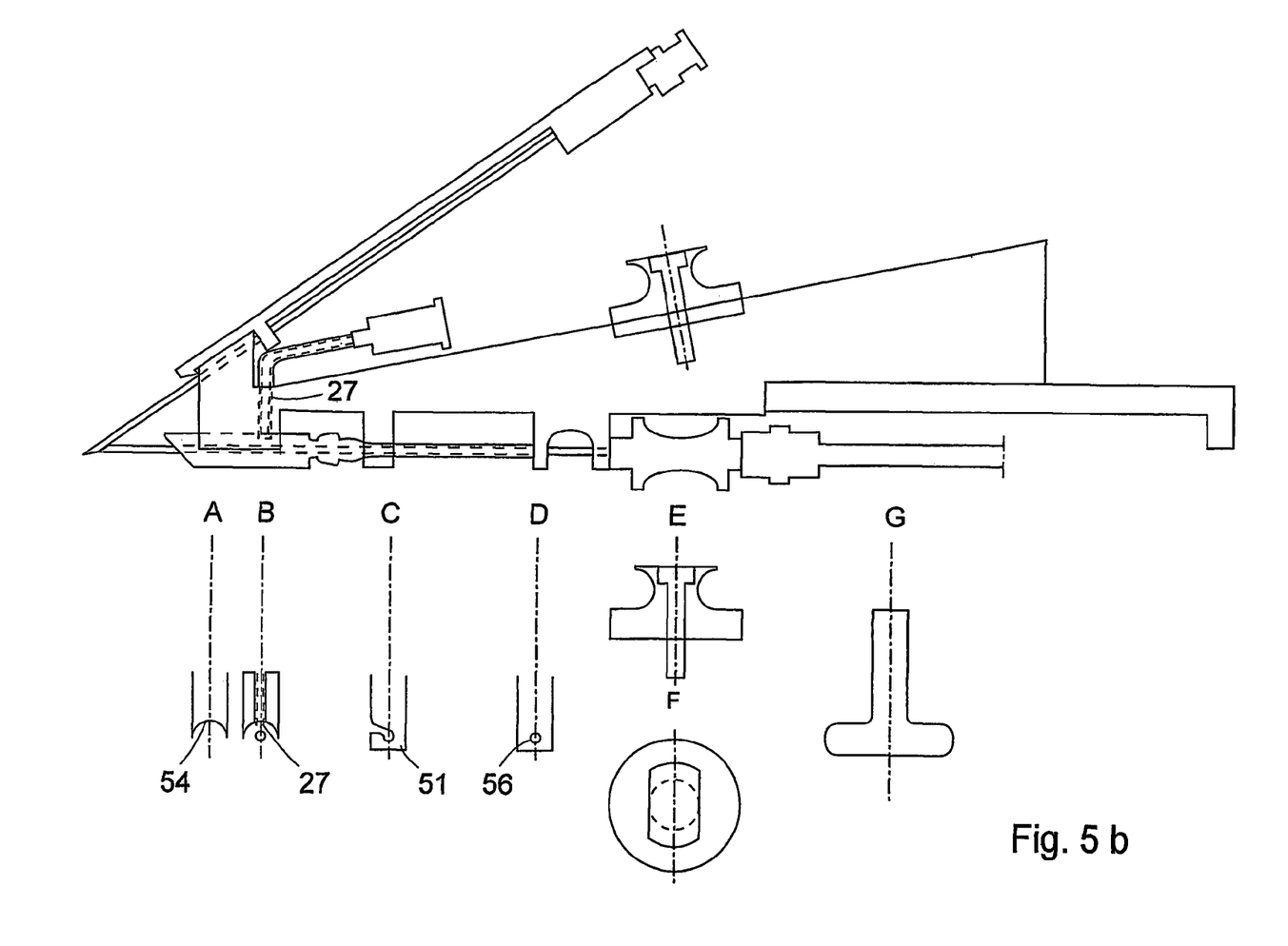
FIG. 5a shows a side view of an applicator of the present invention.
FIG. 5b shows a side view of an applicator of the present invention, with cross-section views A, B, C, D, E, F and G.
Figure 5A:
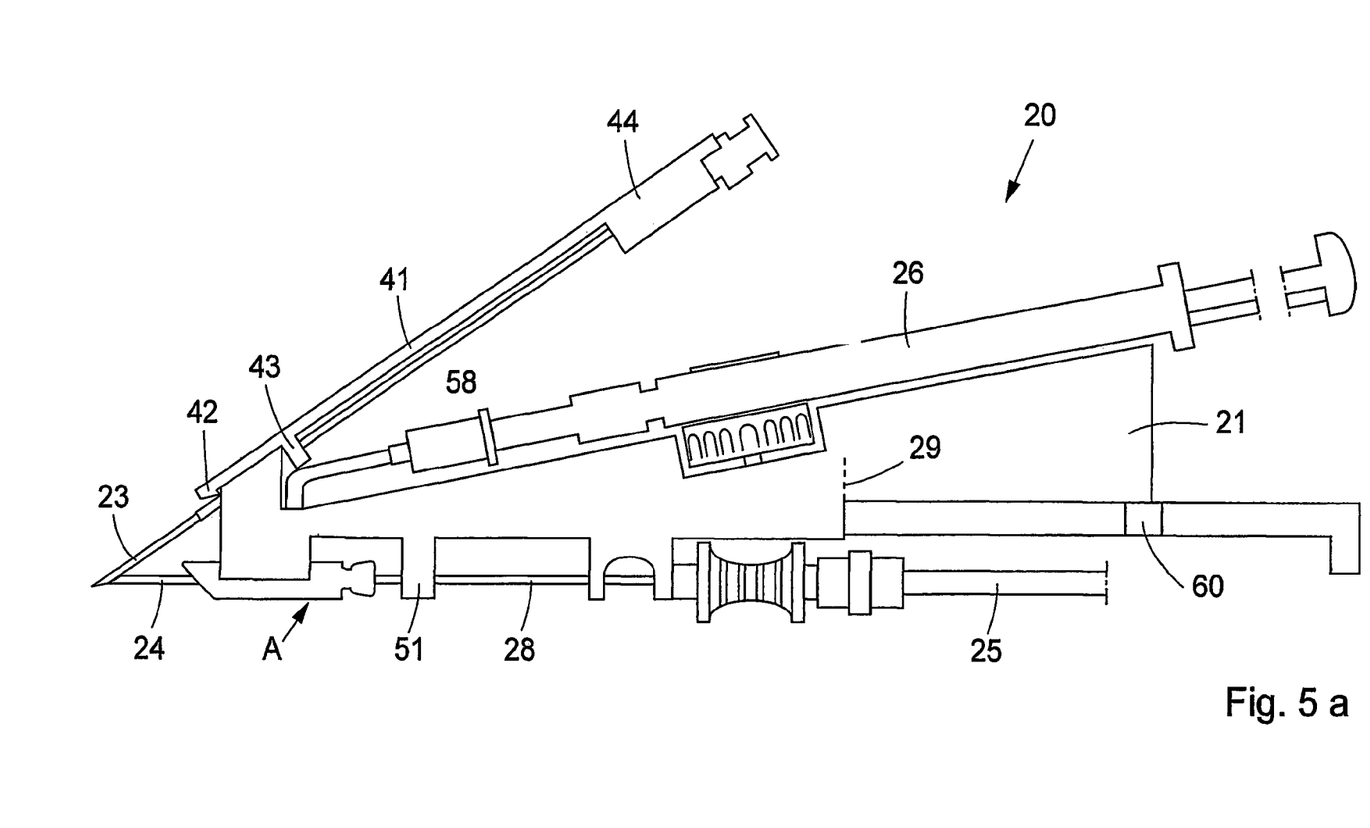

FIG. 5a) shows in a side view, an applicator 20 for applying the device A. The Applicator 20 facilitates the procedure when applying the device A in accordance with the invention on a blood vessel and especially when applying the device A on the deep neck vein when shunting a patient with hydrocephalus.

The applicator 20 consists of a frame 21 made of anodised (eloxidized) aluminium or other suitable material. The frame 21 carries the puncture needle 23, a blunt infusion needle 24 that is connected to a tube 25, a glue conducting tube 27 and the glue syringe 26.

The glue conducting tube 27 is at its lower end arranged for solid and dense connection to the hole 11 of the device, but the device A may still easily be removed. The device A is kept in place on the frame 21 also by help of the force created from the infusion needle 24 and from that said needle is guided by a hook-shaped guide 51. Said guide 51 is advantageously arranged to apply a little force on said infusion needle 24 towards the frame 21 creating a force helping to keep the device A in place at the frame 21. The upper end of the glue conducting tube 27 is arranged to be connected to the glue syringe 26 via its angled needle 58 that has a piece of catheter to prevent leakage.

The puncture needle 23 is fixed to the frame 21 by means of a lock 41. The lock 41 consists of a long, narrow part that has a hook 42 and two small projections 43, 44, each with a hole fitting the puncture needle 23. This lock is arranged to keep the puncture needle 23 in the correct position and yet be easy to remove.

When using the applicator 20 a piece 28 of a silicone catheter is connected to the first end 5 of the inner tube-like part 2 of the device A to prevent leakage. This piece of silicone catheter 28 will later on in the procedure be connected to the catheter from the shunt valve via a connector or be removed to allow the catheter from the shunt valve to be connected directly to the nipple of the device A.

The infusion needle 24 passes through the piece of silicone catheter 28 and through the inner 2 and outer 1 tube-like parts of the device A to a point where it meets the puncture needle 23, that is applied in such a way that the two needles form a sharp angle and the opening of the puncture needle covers the end of the infusion needle. This arrangement allows the infusion needle 24 to be blunt to avoid undue puncturing. The tube 25 that is connected to the other end of the infusion needle 24 is used to check the function of the new channel when the device A is applied on the deep neck vein and the new channel 401 has been created. The infusion needle is withdrawn to a reference point 29 to allow for this check. In this position, the infusion needle ends inside the inner tube-like part 2 close to its second end 6 and the new channel is empty and ready to check for free passage. When the needle is fully retracted, the device A will be released from the applicator 20 and the catheter 28 should then be held with forceps to prevent air embolism or backflow. It is advantageous to provide a mark 60 on the applicator 20 that indicates remaining length of catheter on the infusion needle 24.

The following section will describe how a device according to the invention can be used to connect a CSF conducting catheter to the deep neck vein in a human.

The device A and the applicator 20 are symmetric and their use is independent of whether the person who uses them is right- or left-handed.

FIG. 5b) shows the applicator likewise from the side and also shows a number of cross sections. The figure emphasises on the cross sections of the frame at positions AA to D and G as seen from the left referring to the side view of FIG. 5b. In cross section AA is shown a docking site 54 of the frame 21 for the device A. In cross section B is shown how the glue conducting tube 27 extend into the docking site 54. In C is shown how the hook-shaped guide 51 is arranged for guiding the infusion needle 24 as described above. In D is shown a guide opening 56. The views E and F shows a locking wheel for the (double) syringe seen from two views orthogonal to the side view, i.e., from behind and from above. In G is shown a cross section of the frame at position G having a profile looking like an inverted T.

Figure 6:
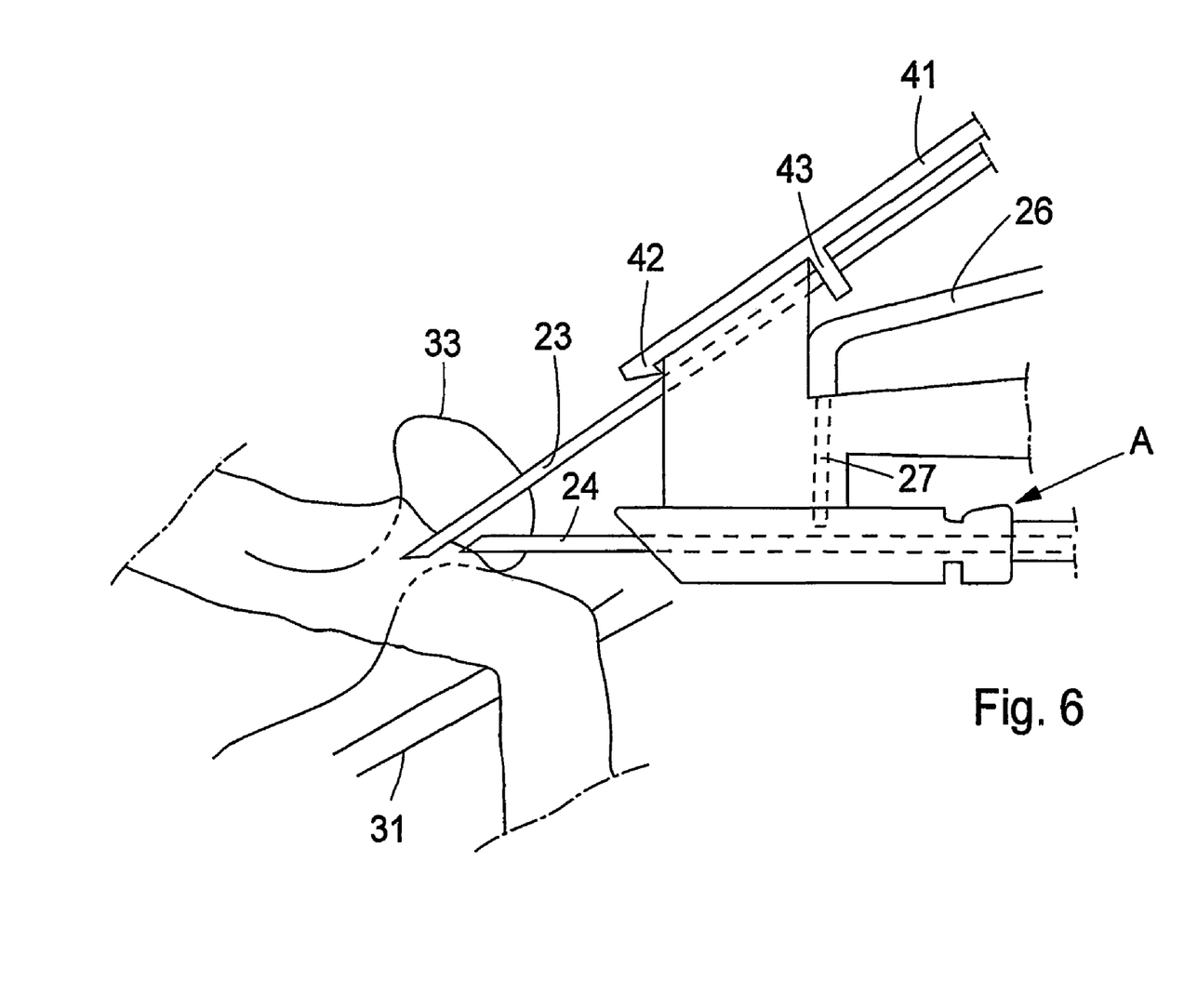
FIG. 6-9 illustrate four steps in the procedure.
Figure 7:
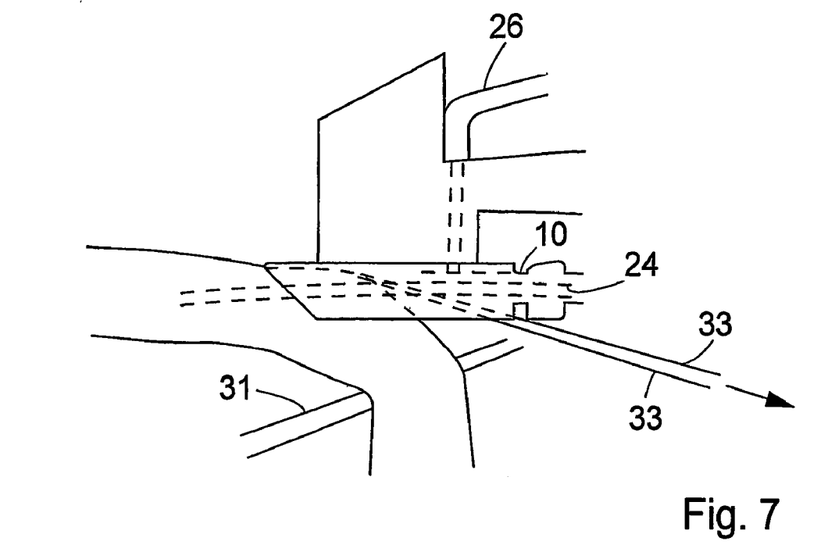

FIG. 6 illustrates the first part of an application procedure. An appropriate length of the deep neck vein is dissected free, lifted and fixed by a support structure 31. The device A can be applied in a direction parallel or anti-parallel to the blood stream. A double suture 33 is placed proximally and distally relatively to the intended puncture site. The puncture will be facilitated by lifting the vessel wall of the vein with the suture needle. After the puncture, the puncture needle 23 is removed FIG. 7 illustrates how the infusion needle 24 with the device A is brought further onto the vein by stretching the suture threads via the lengthwise slit 8 through the cross opening 9 in the opposite direction relatively to the direction of the infusion needle 24. In this way, the inner tube-like part 2 of the device A is passed more easily through the vessel wall of the vein.

The proper position of the vein in the device A can be checked in three ways:

A. The vessel wall of the vein can be seen in the upper cross opening 10.
B. The suture threads should be situated clearly opposite to the upper cross opening 10.
C. The lengthwise slit 8 should to its whole extent be filled with vessel wall.

Figure 8:
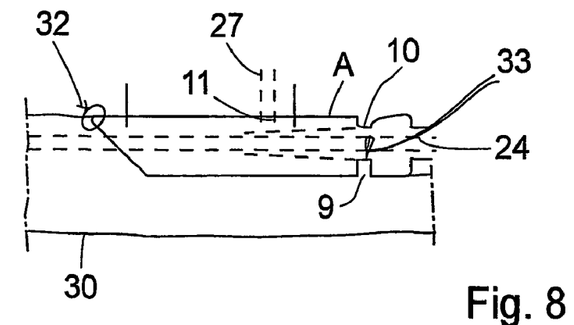

FIG. 8 illustrates that the double suture 33 is tied around the inner tube-like part and by an extra suture incision also around the outer tube. FIG. 8 also shows a suture 32 that attaches the wall of the vein vessel to the device A near the hole 12. When the vein wall is in proper position in the device A and fixed with sutures, glue is injected with force. Glue from the glue syringe 26 is injected via the glue conducting tube 27 through the hole 11 in the outer tube-like part of the device A in such a way that the space between the inside of the outer tube-like part and the vessel wall and all openings are filled with glue. The infusion needle functions as a mould for the new channel that will get the same length as lengthwise slit 8.

Figure 9:
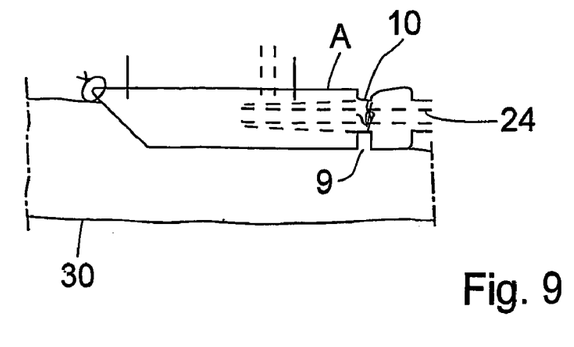

FIG. 9 illustrates the fourth part of the procedure.

When after a few minutes the glue has settled, the glue syringe is removed and the infusion needle 24 is withdrawn to a position where the needle ends inside the inner tube-like part 2 of the device A. Infusion via the infusion needle 24 will now wash out blood from the new channel and its function can be checked. After this, the infusion needle 24 is fully withdrawn and the device A is released from the applicator 20 and can be connected to the catheter coming from the shunt valve.

After possibly adding additional glue on the outside of the device, the wound is sutured to give additional support to the device A.

By means of the device A corresponding to the invention a part of the deep neck vein is now transformed into a narrow, stiff channel with invariable volume. The walls of this channel are living vein walls with good nutrition and the channel is filled with CSF. Backflow of blood in this channel is prevented by the stiff blood vessel walls and by the tightness in the lengthwise slit and by the shunt valve. The new channel has to be narrow (about 1 millimetre in diameter) to allow the small volume of CSF (less than 500 millilitre per 24 h) to remove the blood that mixes with the CSF in the opening into the vein.

Accordingly, this invention makes it possible to drain CSF to the deep neck vein and further to the heart without contact between the fluid-conducting catheter or any foreign material and the blood flow in the vein and at the same time avoid the use of X-ray, ECG or other means to secure the proper position of the catheter in the heart.

The invention also excludes the risk of thrombosis and decreases the risk of infection since neither the device corresponding to the invention, the fluid-conducting catheter or any other foreign material comes in contact with the blood flow in the vein. Draining to the deep neck vein gives a natural antisiphon effect.

Figure 10:
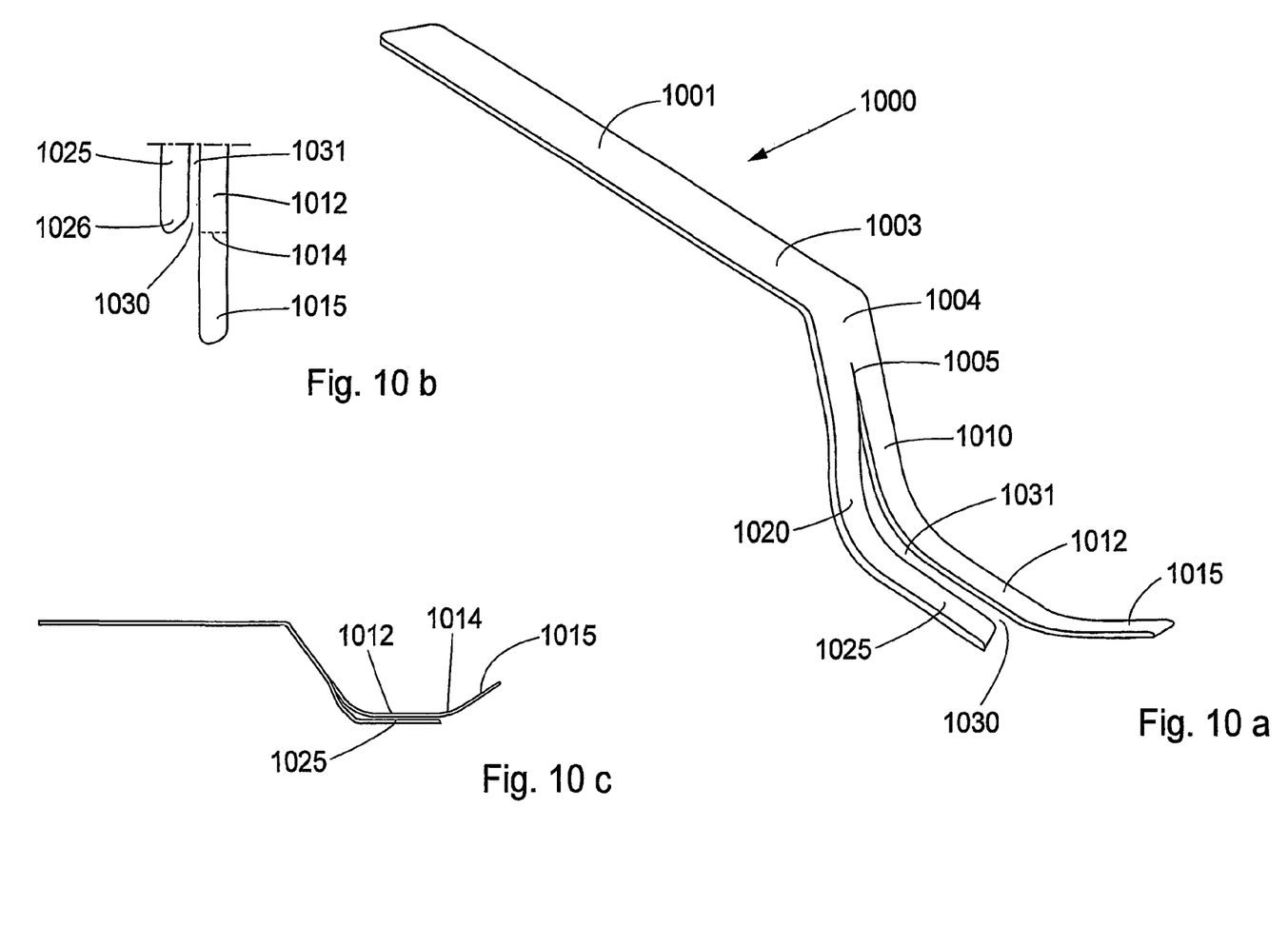

FIG. 10*a*) shows a view of a support, or a support instrument 1000, for supporting fixing and shutting off of a vessel. The support instrument 1000 is especially advantageous for supporting and fixing a neck vein when connecting a hydrocephalus shunt according to an embodiment of the invention to the vein, and the above mentioned support structure 31 in FIG. 6 could advantageously be equal to this support instrument 1000.

An embodiment of the support comprises a handle 1001, a bend 1003, an extending common part 1004, a bifurcation 1005 and two elongated members, one concave or U-shaped 1010, 1012, 1015 and one L-shaped 1020, 1025. The support is preferably devised with essentially flat parts, i.e., at least the common part 1004 and a distal part 1015 of the U-shaped member 1010, 1012, 1015 are devised having essentially rectangular cross sections, with a thickness substantially smaller than a corresponding width. In a typical embodiment the thickness is approximately 0.5 to 2.5 mm and the width of the common part is approximately 5 to 15 mm.

The support is devised for capturing a blood vessel between the U-shaped member 1015 and the L-shaped member 1025, in the opening 1030 that is formed between said members; said opening 1030 continues as a lengthwise slit 1031 between said members 1012, 1025. Said lengthwise slit, 1031 between these members has essentially a width corresponding to the double thickness of the blood vessel wall for the vessel in question, i.e., embodiments of the support instrument provides different sizes of said slit, and of course also of the instrument itself. The reason for having a slit of that dimensions is that when a vessel is captured in the slit, the vessel is flattened and compressed so that the blood-flow is reduced. Typical widths include 1 to 1.5 mm. The reduction is in most cases complete so that the blood flow is shut off. The U-shaped and the L-shaped members preferably have a rectangular or quadratic cross section, and are so arranged that said opening 1030 and slit formed between the portions 1012 and 1025 is wide enough to let the vessel slide gently into place when the support is twisted a bit. The members have rounded edges, so that the risk of hurting the vessel or other tissues during proper use of the support instrument is reduced or eliminated. The opening 1030 is preferably arranged so that a free end 1026 of the member 1025 are placed opposite a bend 1014 between the distal parts of the U-shaped member 1012, 1015. Said free end 1026 is triangularly shaped so that the opening 1030 is wide at start and narrows as it transitions to the slit 1031.

The support is devised to lock itself into place at the operating wound as the distal part of the U-shaped member and the common part 1004 or the part of the U-shaped and L-shaped members 1010, 1020 immediately following the bifurcation 1005 are arranged to make contact to the wound edges, and because the cross section of said members and part is flat or rectangular. Because the vessel itself, when caught in the slit between the members 1025, 1012 or just resting above both members, will exert a certain force on the support instrument 1000 directed downwards to the bottom of the operating wound, the instrument will come neatly into place.

The invention claimed is:

1. A device for conducting fluid from a fluid-conducting catheter to a blood vessel comprising:
    an outer tube-like part with a first and a second end; and
    an inner tube-like part with a first and a second end,
      which tube-like parts are arranged with essentially parallel axes and joined with each other at or close to the first end of the outer tube-like part and at a portion of the inner tube-like part, and
    where the outer tube-like part, along a part of its length, extending from its second end is provided with a lengthwise slit for reception of a part of the blood vessel; and
    wherein the first end of the inner tube-like part is arranged to be connected to the fluid-conducting catheter and the second end of the inner tube-like part is wholly or partly enclosed by said outer tube-like part, and is arranged to cross the blood vessel wall.

2. A device for conducting fluid from a fluid-conducting catheter to a blood vessel comprising:
    an outer tube-like part with a first and a second end, and
    an inner tube-like part with a first and a second end, wherein said tube-like parts are arranged with essentially parallel axes and joined with each other at or close to the first end of the outer tube-like part and at a portion of the inner tube-like part, and wherein the outer tube-like part, along a part of its length, extending from its second end is provided with a lengthwise slit for reception of a part of the blood vessel, wherein the lengthwise slit has a width that essentially corresponds to double the thickness of the blood vessel wall, and wherein the first end of the inner tube-like part is arranged to be connected to the fluid conducting catheter and the second end of the inner tubelike part is wholly or partly enclosed by said outer tube-like part, and is arranged to cross the blood vessel wall.

3. The device according to claim 2, wherein the outer tube-like part further comprises an internal thread at or close to its first end, and the inner tube-like part further comprises an external thread at the portion of the inner tube-like part, wherein said external thread corresponds to said internal thread, and wherein said joined outer and inner tube-like parts are joined by the internal thread and corresponding external thread.

4. The device according to claim 2, wherein the outer tube-like part further comprises an internal conical form at or close to its first end, and the inner tube-like part further comprises a conical form at the portion of the inner tube-like part, wherein said internal conical form corresponds to said conical form at the portion of the inner tube-like part, and wherein said joined outer and inner tube-like parts are joined by the conical form at the portion of the inner tube-like part and the corresponding internal conical form.

5. The device according to claim 2, wherein the outer and the inner tube-like parts are integrated.

6. The device according to claim 2, wherein the second end of the outer tube-like part is cut at an angle in such a way that the side with the lengthwise slit of the outer tube-like part is the shortest.

7. The device according to claim 2, wherein the outer tube-like part is devised with a first and a second opening close to its first end wherein the first opening is joined with and is transversal to the lengthwise slit, and where the second opening is situated essentially diametrically opposite the first opening.

8. The device according to claim 2, wherein the outer tube-like part at its second end further comprises at least one hole for suturing the device to the blood vessel.

9. The device according to claim 2, wherein the outer tube-like part is provided with a hole, and wherein said hole is for at least one entry of glue and temporary fixation of the device to an applicator instrument.

10. The device according to claim 2, wherein the device is made of a solid tissue compatible material.

11. The device according to claim 10 wherein the solid tissue compatible material is polyetheretherketone.

12. A device for conducting fluid from a fluid-conducting catheter through the device to a blood vessel comprising:

an outer tube-like part with a first and a second end, and an inner tube-like part with a first and a second end, wherein the outer tube-like part and the inner tube-like part are arranged with substantially parallel axes and are joined with each other at or close to the first end of the outer tube-like part and at a portion of the inner tube-like part, and wherein the outer tube-like part, along a part of its length, extending from its second end, is provided with a lengthwise slit for reception of a part of the blood vessel and wherein said lengthwise slit has a width that essentially corresponds to the double thickness of the wall of the blood vessel, and wherein the first end of the inner tube-like part is arranged to be connected to the fluid-conducting catheter and the second end of the inner tube-like part is wholly or partly enclosed by said outer tube-like part, and is arranged to cross the blood vessel wall, and wherein the device when applied to the blood vessel is to be secured to the outside of the blood vessel, partly penetrating into the blood vessel, and wherein the device when applied to the blood vessel forms a channel in a part of the length of the blood vessel, which channel runs essentially parallel with the vessel, and wherein neither the device when applied to the blood vessel nor the fluid-conducting catheter are in contact with the blood flow in the blood vessel.

* * * * *